(12) United States Patent
Tsukashima et al.

(10) Patent No.: US 11,723,745 B2
(45) Date of Patent: Aug. 15, 2023

(54) CANNULA AND PROXIMALLY MOUNTED CAMERA WITH AN IMAGING CONTROL SYSTEM FOR ROTATING IMAGES

(71) Applicant: Rebound Therapeutics Corporation, Irvine, CA (US)

(72) Inventors: Ross Tsukashima, Irvine, CA (US); Peter G. Davis, Irvine, CA (US); Robert Flower, Irvine, CA (US); Milo A. Amorsolo, Irvine, CA (US)

(73) Assignee: Rebound Therapeutics Corporation, Irvine, CA (US)

(*) Notice: Subject to any disclaimer, the term of this patent is extended or adjusted under 35 U.S.C. 154(b) by 742 days.

(21) Appl. No.: 16/706,530

(22) Filed: Dec. 6, 2019

(65) Prior Publication Data
US 2020/0179078 A1   Jun. 11, 2020

Related U.S. Application Data

(60) Provisional application No. 62/776,055, filed on Dec. 6, 2018.

(51) Int. Cl.
| | |
|---|---|
| *A61B 90/00* | (2016.01) |
| *A61B 17/34* | (2006.01) |
| *A61B 34/20* | (2016.01) |
| *G06T 3/60* | (2006.01) |

(52) U.S. Cl.
CPC .......... *A61B 90/37* (2016.02); *A61B 17/3421* (2013.01); *A61B 34/20* (2016.02); *A61B 90/361* (2016.02); *G06T 3/60* (2013.01); *A61B 2034/2048* (2016.02); *A61B 2034/2068* (2016.02); *A61B 2034/2074* (2016.02); *A61B 2562/0219* (2013.01)

(58) Field of Classification Search
None
See application file for complete search history.

(56) References Cited

U.S. PATENT DOCUMENTS

| | | | |
|---|---|---|---|
| 6,361,488 B1* | 3/2002 | Davison | A61B 90/50 600/102 |
| 9,931,025 B1* | 4/2018 | Graetzel | A61B 90/06 |
| 10,105,042 B2* | 10/2018 | Davis | A61B 90/361 |
| 10,172,525 B2* | 1/2019 | Davis | A61B 5/6886 |

(Continued)

FOREIGN PATENT DOCUMENTS

| | | |
|---|---|---|
| JP | H06269406 | 9/1994 |
| KR | 1020100112309 | 10/2010 |
| KR | 101500717 | 3/2015 |

OTHER PUBLICATIONS

International Search Report from IA PCT/US2019/065076 dated Apr. 8, 2020.

(Continued)

*Primary Examiner* — Kaitlin A Retallick
(74) *Attorney, Agent, or Firm* — Crockett & Crockett, PC; K. David Crockett, Esq.

(57) ABSTRACT

A cannula system with a proximally mounted camera assembly, sensors or sensor pair component(s), radially fixed to the camera assembly and an image control system operable to rotate image data obtained from the camera for display on a display screen, to maintain an image in an orientation preferred by a surgeon even as the camera assembly is rotated radially about the axis of the cannula.

3 Claims, 4 Drawing Sheets

(56) References Cited

U.S. PATENT DOCUMENTS

| | | | |
|---|---|---|---|
| 10,398,318 B2* | 9/2019 | Davis | A61B 5/1473 |
| 10,413,169 B2* | 9/2019 | Davis | A61B 1/05 |
| 11,284,890 B2* | 3/2022 | Nalagatla | A61B 17/072 |
| 2003/0016883 A1 | 1/2003 | Baron | |
| 2004/0059217 A1 | 3/2004 | Kessman | |
| 2005/0027167 A1* | 2/2005 | Chatenever | A61B 1/00045 |
| | | | 600/173 |
| 2014/0005486 A1 | 1/2014 | Charles | |
| 2017/0143191 A1 | 5/2017 | Haraguchi et al. | |
| 2017/0265879 A1 | 9/2017 | Washburn, II et al. | |
| 2017/0332887 A1 | 11/2017 | Davis et al. | |
| 2017/0332912 A1* | 11/2017 | Tsukashima | A61B 1/00052 |
| 2022/0225868 A1* | 7/2022 | Davis | A61B 17/3421 |

OTHER PUBLICATIONS

Extended European Search Report dated Jul. 8, 2022 from European Patent Application No. 19893447.3.

* cited by examiner

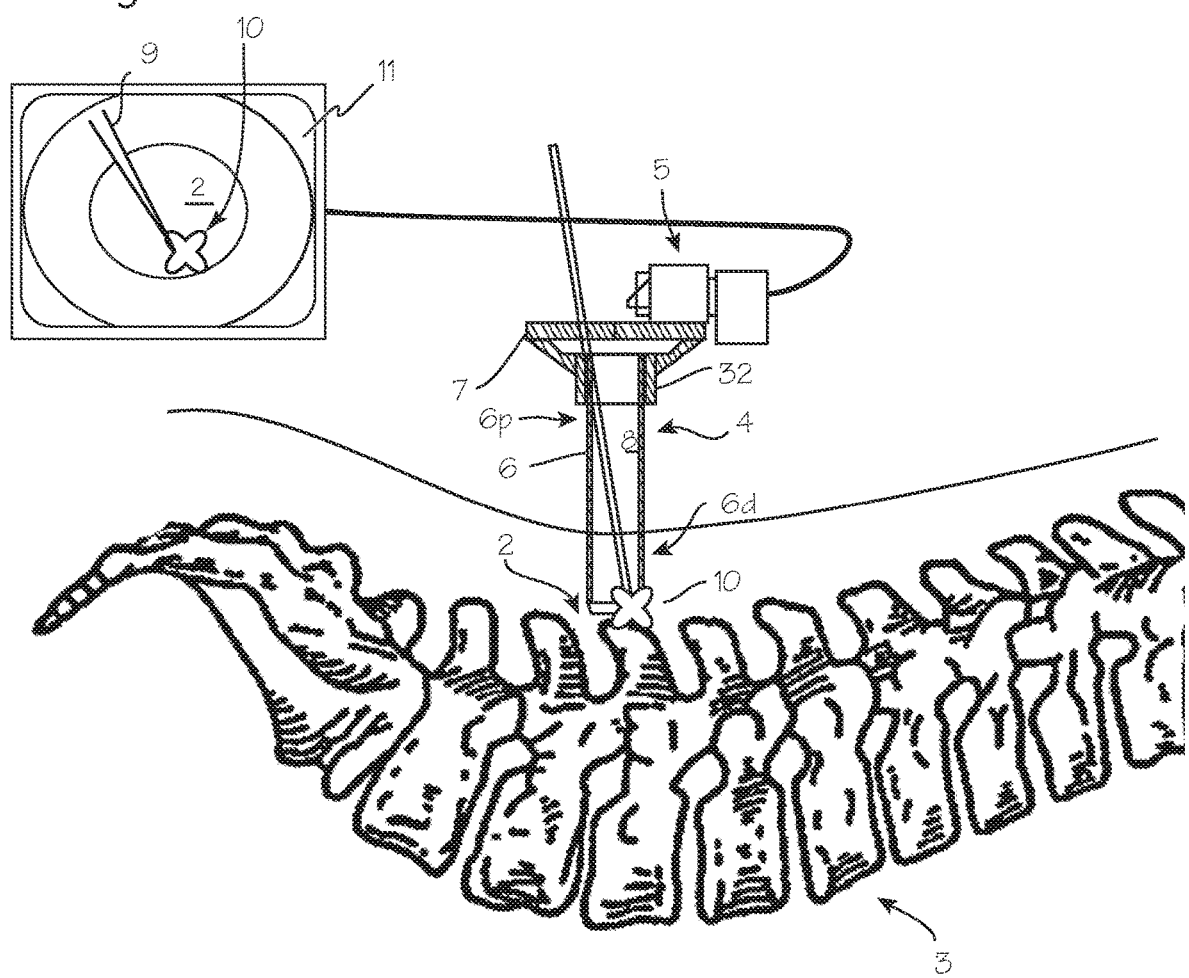

Original view

Uncorrected view with camera and cannula rotated

Corrected view with camera and cannula rotated

CANNULA AND PROXIMALLY MOUNTED CAMERA WITH AN IMAGING CONTROL SYSTEM FOR ROTATING IMAGES

This application claims priority to U.S. Provisional Application 62/776,055 filed Dec. 6, 2018, pending.

FIELD OF THE INVENTIONS

The inventions described below relate to the field of minimally invasive surgery.

BACKGROUND OF THE INVENTIONS

U.S. patent application Ser. No. 15/239,632, entitled Cannula with Proximally Mounted Camera (filed Aug. 17, 2016) discloses a cannula system with a proximally mounted camera, operable to obtain images at the distal end of a cannula tube with a camera located entirely proximally of the proximal edge of the cannula tube. The camera (or a component of a camera assembly) extends slightly into the cylindrical space defined by the cannula tube and extending proximally from the cannula tube, to overhang the lumen of the cannula tube, such that the surgeon using the system camera may need to rotate the camera, or the entire camera and cannula assembly, to make room for surgical tubes otherwise impeded by the overhanging camera. The system may be used for spine surgery, brain surgery or other procedures.

SUMMARY

The devices and methods described below provide for improved visualization of body tissue during minimally invasive surgery, including spine surgery and brain surgery. The device comprises a cannula with a camera, or camera component, mounted on the proximal end of the cannula with a view into the cannula lumen and the tissue within and below the lumen. A prism, reflector or other suitable optical element oriented between the camera and the lumen of the cannula may be included to afford the camera a view into the cannula while minimizing obstruction of the lumen. The camera or optical element is small, relative to the cannula tube, so that long, small diameter surgical tools may be inserted through the cannula to locate the distal tip of the tools in a surgical space at the distal end of the cannula. The system includes means for adjusting the displayed image, to rotate the displayed image to an initial preferred "natural" orientation for the surgeon, regardless of the radial position of the camera (if an initial placement does not provide a display in a preferred orientation). The system also includes means for tracking the radial position of the camera, relative to the tube of the cannula or relative to an initial position in space, and an imaging control system for rotating the image, in response to rotation of the camera about the proximal end of the cannula tube, to continue to present an image of the surgical space in the initial preferred orientation.

The system, and the method of access it enables, may be used in minimally invasive surgery to provide an image of a surgical space to a surgeon in an orientation preferred by the surgeon while the surgeon is manipulating long surgical tools within the cannula, and observing the workspace and tool tips on a large display screen located near the patient. The preferred orientation will most likely be (for a surgeon standing vertically beside the patient) an orientation that presents the image of the surgical space in a "natural" up-down orientation from the surgeon's perspective, with the portion of the surgical space furthest from the surgeon at the top of the displayed image, the portion of the surgical space nearest the surgeon at the bottom of the displayed image, the portion of the surgical space at the surgeon's right displayed at the right side of the displayed image, and the portion of the surgical space at the surgeon's left displayed at the left side of the displayed image. The surgeon may place the cannula in the patient, with the distal end of the cannula proximate the surgical space, and with the camera at any radial position relative to this natural up-down orientation, and adjust the image using controls provided in the image presentation system, to rotate the displayed image to match the natural up-down orientation (or any other preferred orientation). Thereafter, the surgeon may rotate the camera (or the entire cannula and camera assembly) as necessary to manipulate the tools disposed within the cannula tube, and the image display system may be operated to sense the rotation of the camera (or the entire cannula and camera assembly), and "counter-rotate" the image to maintain the displayed image in the natural up-down orientation (or any other preferred orientation).

The system and method are illustrated in relation to spinal surgery. The system and method may be used in brain surgery and other surgeries.

BRIEF DESCRIPTION OF THE DRAWINGS

FIG. 2 illustrates a cannula with a proximally mounted camera.

DETAILED DESCRIPTION OF THE INVENTIONS

Figure 1:
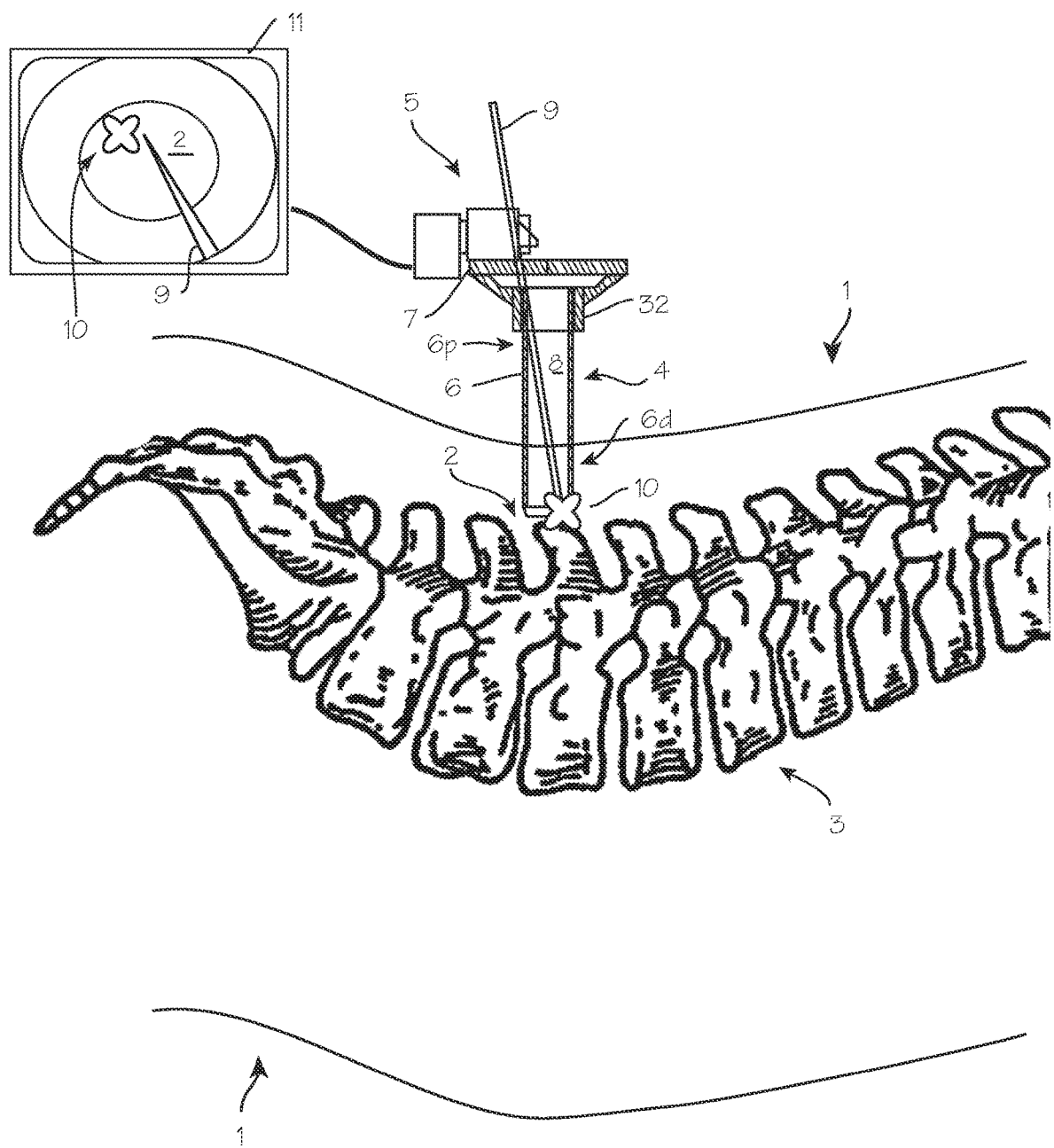
FIG. 1 illustrates a patient with an area requiring surgical intervention, and a cannula and camera system installed through an incision to place the distal tip of the cannula tube near the spine of the patient.

FIG. 1 illustrates a patient 1 with target tissue 2 proximate the spine 3 that necessitates surgical intervention. A cannula 4 has been inserted through a surgical opening, with the distal end of the cannula proximate target tissue on the spine. The target tissue may be a vertebral disc, bones of the spine, or other tissue or a foreign object. A camera 5 is mounted on the proximal rim of the cannula, with a portion of the camera overhanging the rim of the cannula and disposed over the lumen of the cannula, and is operable to obtain video or still images of the blood mass or other tissue at the distal end of the cannula. The cannula may comprise a cannula tube 6 and a mounting structure 7 may be used to secure the camera to the proximal end 6p of the cannula, to provide a view through the lumen 8 of the cannula tube.

As shown in FIG. 1, a surgical tool 9 is disposed within the cannula tube, in order to perform some operation on some tissue portion 10 of the target tissue 2 within the surgical space. This tissue might, for example, be a protruding vertebral disc to be trimmed (a mini-discectomy), or a portion of a pedicle or transverse process to be excised or secured to implants, or a tumor or other diseased tissue to be ablated or removed, etc. The image display system is operated to display the image obtained by the camera, and shows an image of the body tissue on the display screen in an initial preferred orientation. (The image display system comprises the display screen 11 and an image control system operable to receive image signals from the camera, receive position signals from the sensors, and transmit image data to the display screen, rotated as directed by the user). In this example, an image of the target tissue 2 appears within the annular image of the inside wall of the cannula, and the tissue portion 10 appears at the top of the screen, because it is furthest from the surgeon and the surgeon has selected this as the preferred initial orientation. An image of the surgical tool 9 also appears on the display screen. However, due to the position of the camera, the surgeon may not be able to attack the tissue portion with full confidence, and may not be able to clearly see the tissue to be approached due to the presence of the proximal portions of the tool in the field of view which block the view of the tissue portion 10 of concern. To address this, the surgeon may rotate the camera about an axis of the cannula tube (either by rotating the entire cannula and camera assembly or rotating the camera about the cannula tube, without rotating the camera tube). This rotation is shown in FIG. 2. Without correction, this rotation will flip the displayed image, and the tissue portion 10 will appear at the bottom of the displayed image (and left and right in the image will be reversed).

While it is possible to perform the surgical procedure while viewing the surgical space upside down and reversed, it is more natural, and thus safer, to operate on the spine with the assistance of a consistent image display. Accordingly, the image display system is operable to receive signals corresponding to radial position and/or radial motion from the position sensors associated with the camera, determine an initial position relative to the cannula or an absolute initial position in space based on those signals, and thereafter determine the radial position of the camera vis-à-vis a previously determined initial position relative to the cannula or an absolute initial position in space, and generate a "counter-rotated" image and display the counter-rotated image on the display screen in the initial preferred orientation, so that the surgeon may operate, regardless of camera position, on the basis of a displayed image which is consistent throughout the procedure.

Figure 3A:
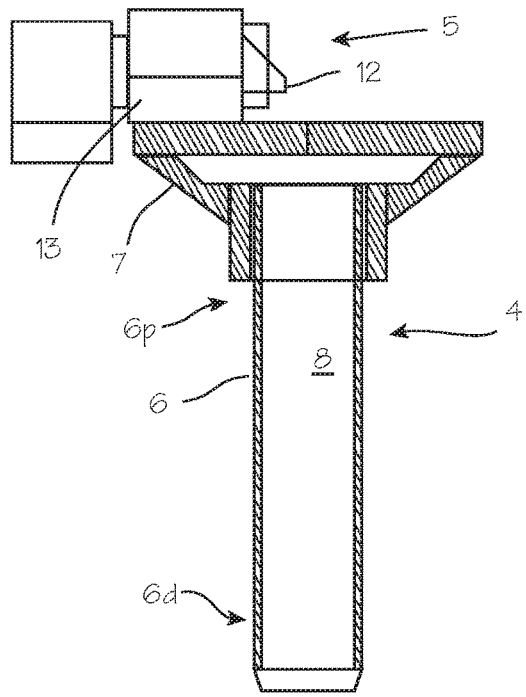
FIGS. 3A, 3B and 3C illustrate the cannula and camera system with sensors to operable to generate signals corresponding to the radial position of the camera.
Figure 3B:
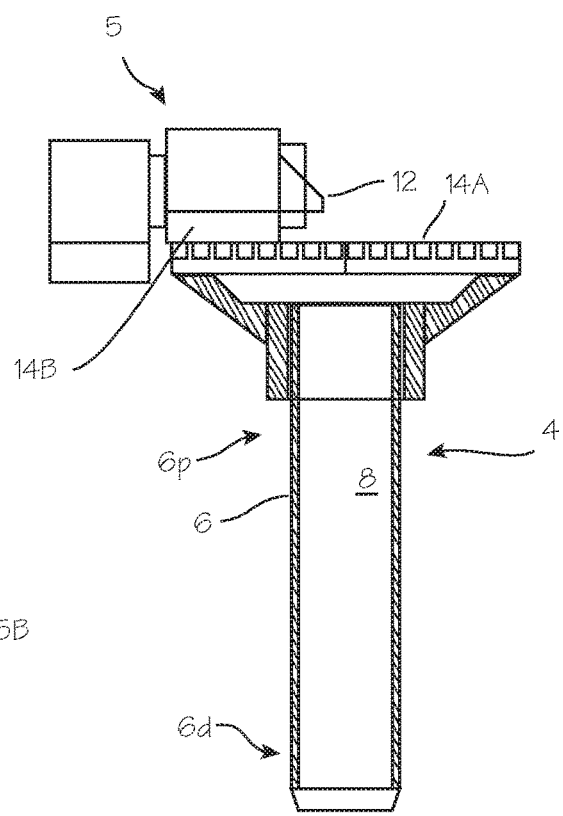
Figure 3C:
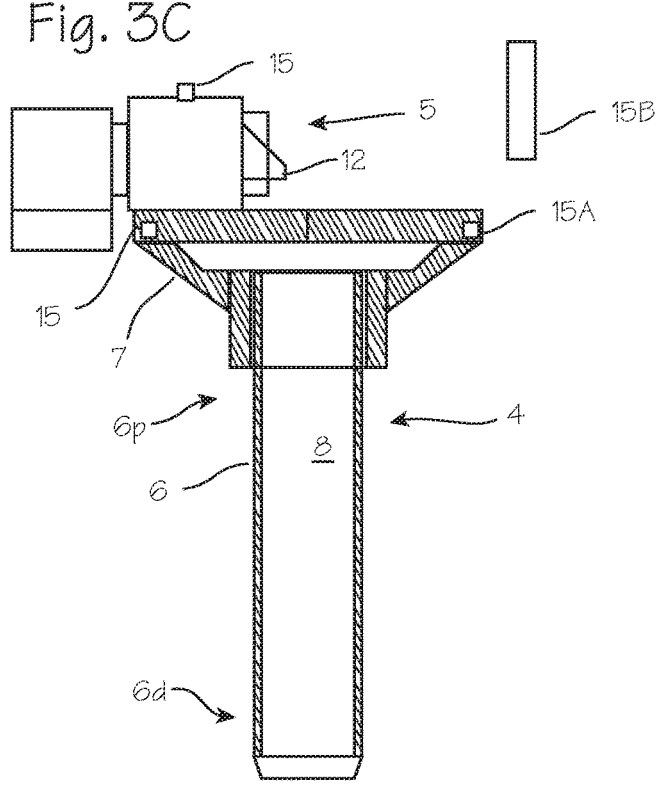

FIGS. 3A, 3B and 3C illustrate the cannula and camera system with sensors operable to generate signals corresponding to the radial position of the camera. As shown in FIG. 3A, 3B and 3C, the cannula 4 includes the components shown in FIGS. 1 and 2, including the cannula tube 6 mounting structure 7, and the system further includes the camera assembly 5 with a component, such as a prism, a reflector or other mirror structure or optical element 12, overhanging the lumen of the cannula tube. The several views depict several of the many sensors that may be used, in conjunction with the image control system, to determine the radial position of the camera relative to the cannula tube.

FIG. 3A depicts a gyroscope or an accelerometer assembly 13 (a single accelerometer, or a multi-axis axis accelerometer assembly) radially fixed to the camera assembly. The camera assembly in this embodiment may be rotatable on the mounting structure, or radially fixed to the mounting structure and/or cannula tube, or it may be rotatable relative to the cannula tube, through the mounting ring which is mounted on the end of the cannula tube using an annular snap fitting and corresponding detent on the cannula tube, a threaded fitting, a rotary union, or other means for rotatable attachment.

The sensor is operable to provide a signal to the image control system corresponding to motion of the camera assembly, and the image control system is configured to receive input from a user indicating that the camera is in a first radial position (corresponding, for example, to an initial orientation or an initial preferred orientation) and display an image of the surgical field in a first orientation corresponding to the first radial position on the display screen, and thereafter receive signals corresponding to motion of the camera assembly, and determine the radial position of the camera relative to the first radial position, and, based on this determination, rotate the image presented on the display screen to present an image in the initial orientation or an initial preferred orientation.

The sensor is operable to provide a signal to the image control system corresponding to motion of the camera assembly, and the image control system is configured to receive input from a user indicating that the camera is in a first radial position (corresponding, for example, to an initial orientation or an initial preferred orientation) and display an image of the surgical field in a first orientation corresponding to the first radial position on the display screen, and thereafter receive signals corresponding to motion of the camera assembly, and determine the radial position of the camera relative to the first radial position, and, based on this determination, rotate the image presented on the display screen to present an image in the initial orientation or an initial preferred orientation.

FIG. 3B depicts an encoder assembly (encoder scale 14A and a reader 14B) radially fixed to the camera assembly. The camera assembly in this embodiment is rotatable on the mounting structure, and the mounting structure is radially fixed to the cannula tube. A first component of the encoder assembly (an encoder reader) 14A is fixed to the camera, and a second component of the encoder assembly (an encoder scale) 14B is fixed to the mounting structure.

The encoder assembly is operable to provide a signal to the image control system corresponding to the position of the camera assembly on the mounting structure, and the image control system is configured to receive input from a user indicating that the camera is in a first radial position (corresponding, for example, to an initial orientation or an initial preferred orientation) and display an image of the surgical field in a first orientation corresponding to the first radial position on the display screen, and thereafter receive signals corresponding to a second position (or the motion of the camera) of the camera assembly, and determine the radial position of the camera relative to the first radial position, and, based on this determination, rotate the image presented on the display screen to present an image in the initial orientation or the initial preferred orientation.

FIG. 3C depicts a neuronavigation marker array 15 radially fixed to the camera assembly. The camera assembly in this embodiment may be rotatable on the mounting structure, or radially fixed to the mounting structure and/or cannula tube. The neuronavigation marker array is a first component of the neuronavigation system 15A is fixed to the camera, and a second component of the neuronavigation system (sensor(s) operable to detect the markers, such as cameras, antennas, ultrasound sensors, etc.) 15B is disposed proximate the marker array.

The neuronavigation system is operable to provide a signal to the image control system corresponding to the position of the camera assembly on the mounting structure, and the image control system is configured to receive input from a user indicating that the camera is in a first radial position (corresponding, for example, to an initial orientation or an initial preferred orientation) and display an image of the surgical field in a first orientation corresponding to the first radial position on the display screen, and thereafter receive signals corresponding to a second position (or the motion of the camera) of the camera assembly, and determine the radial position of the camera relative to the first radial position, and, based on this determination, rotate the image presented on the display screen to present an image in the initial orientation or the initial preferred orientation.

Generally, the image control system is configured to receive input from a user indicating that the camera is in a first radial position and display an image of the surgical field in an initial orientation corresponding to the first radial position on the display screen, and thereafter receive signals from the sensors corresponding to the radial position of the camera assembly, and determine the radial position of the camera relative to the first radial position, and, based on this determination, rotate the image presented on the display screen to present an image in the initial orientation or an initial preferred orientation. (The first radial position can be defined by a geometric home position where the camera may only be attached to the cannula in an initial radial position or it may be initiated through the image control system software user control setting a "home" or "origin" starting position.)

The position sensors may be provided in many forms, including the encoder operable to provide a signal corresponding to the radial position of the camera relative to the cannula tube, or other position counters (able to count circular marks surrounding the top of the cannula) or color arrays surrounding the cannula and interpreting the camera position based on the software; a rheostat operable to provide a signal corresponding to the radial position of the camera relative to the tube; a gyroscope, operable to provide a signal corresponding to motion of the camera about the plane defined by the mounting structure or proximal edge of the cannula tube (or a plane perpendicular to the long axis of the cannula tube), which may be interpreted by the image control system to determine radial displacement of the camera from an initial position; an accelerometer assembly, operable to provide a signal corresponding to radial motion of the camera about the plane defined by the mounting structure or proximal edge of the cannula tube (or a plane perpendicular to the long axis of the cannula tube), which may be interpreted by the image control system to determine radial displacement of the camera from an initial position; neuronavigation markers, which, together with a neuronavigation system may provide a signal corresponding to radial motion of the camera about the cannula tube; a combination of accelerometers, gyroscopes and gravitational sensors which are operable to provide signals corresponding to absolute position and orientation of the camera, which may be interpreted by the image control system to determine radial displacement of the camera from an initial position; and any other means for sensing the position of the camera, or generating signals corresponding to the radial position of the camera assembly, relative to an axis of the cannula tube, either vis-à-vis a previously determined initial position relative to the cannula or an absolute initial position in space.

Figure 4:
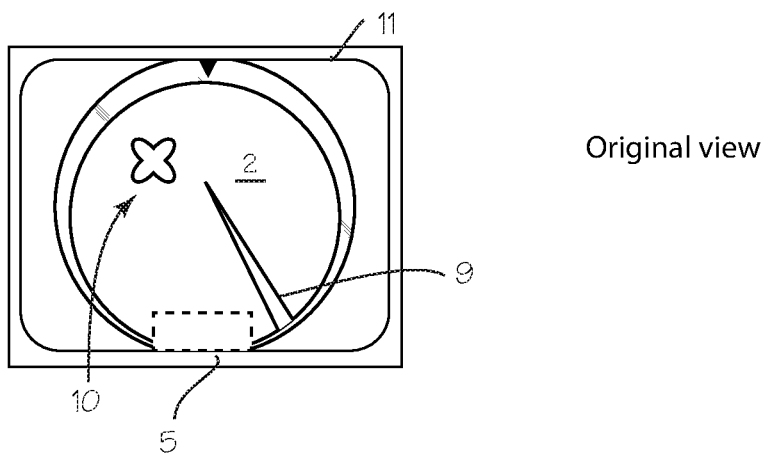
FIGS. 4, 5 and 6 depict exemplary images obtained by the camera with an image in a first preferred orientation, a disfavored rotated orientation, and a second preferred orientation image created by the image control system in response to a determination of the change in radial position of the camera.
Figure 5:
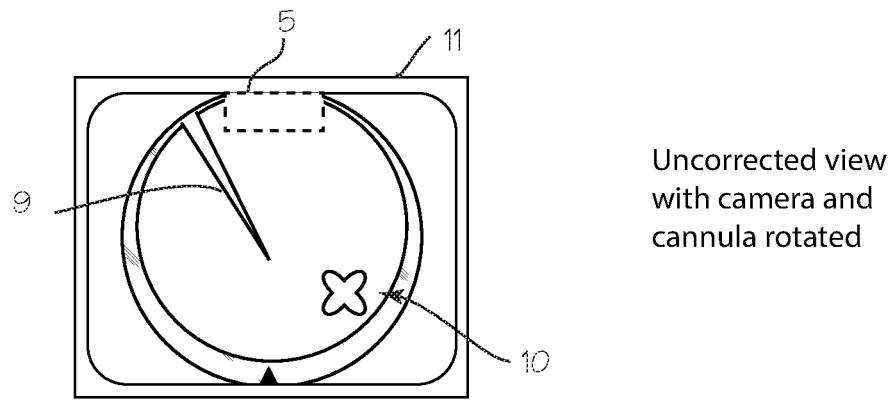
Figure 6:
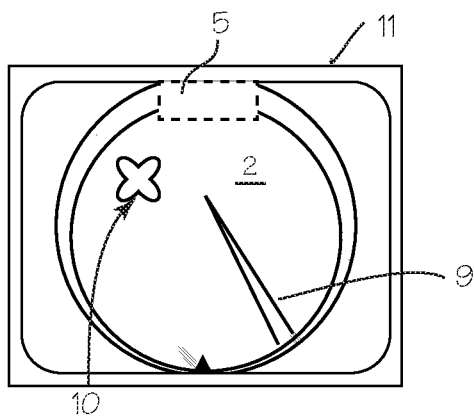

FIGS. 4, 5 and 6 depict exemplary images obtained by the camera with an image in a first preferred orientation, a disfavored rotated orientation, and a second preferred orientation image created by the image control system in response to a determination of the change in radial position of the camera. In FIG. 4, the camera is in an initial radial position, which in this case has been set by the surgeon as a preferred orientation by providing input to the image control system. The position of the camera and prism, relative to the image, is shown in phantom. This image may be (1) the image obtained by initial placement of the cannula, including manual rotation of the camera or cannula, or (2) software rotation of the image to present an image in the preferred rotation. In this image of FIG. 4, the camera is located at the bottom of the screen (a default of the system; the system may be configured to provide a default view of any orientation), and includes an image of target tissue 2, surrounded by an annular image of the inside wall of the cannula tube 6, with an image of the tissue portion 10 at the upper left of the image (about 11:00 position) because the tissue portion is opposite to the radial position of the camera, which is at the 6:00 position. The tool 9 appears extending down from the proximal end of the cannula, towards the tissue portion 10. This image of the first preferred orientation will be rotated if the surgeon rotates the camera to move the camera out of its obstructing position (for example, if the surgeon has rotated the cannula and camera system about 180°). This rotation is shown in FIG. 5, which shows the tissue portion at the lower right, at about the 5:00 position, clockwise relative to the camera (which is now at the top of the image, at the 12:00 position). With this rotated image, the surgeon may have difficulty interpreting the image. The image control system is operable, at the selection of the surgeon, to rotate the image on the display back to the initial preferred orientation, as shown in FIG. 6. With this corrected display, the surgeon may manipulate the tool to attack the tissue portion 10, using a display in which the display is presented in the natural orientation, with tissue furthest from the surgeon shown at the top of the display and tissue closest to the surgeon shown at the bottom of the screen.

In use, a surgeon will insert the distal end 6d of the cannula tube into the body of a patient, through a surgical opening (or a natural opening), to place the distal end proximate the target tissue 2 and the tissue portion 10 to be treated, inspected, etc. The surgeon will initially place the camera at a convenient radial location relative to the opening, the patient's position and the surgeon's stance. The surgeon will provide input to the image control system through an input means, indicating that this radial position is a first radial position, and the image control system will then display an image of the surgical field in an initial orientation corresponding to the first radial position on the display screen. If the surgeon is satisfied with this image, the surgeon will provide input to the image control system through an input means indicating that this is an initial preferred orientation. If the surgeon prefers a different initial preferred orientation, the surgeon may provide input to the image control system to rotate the image (maintaining the camera in its initial radial position) to a desired initial preferred orientation, and provide input to the system indicating that the resultant orientation of the image is the initial preferred orientation. Thereafter, the surgeon may operate the image control system to receive input from the sensors which are indicative of the radial position of the camera (vis-à-vis the initial position), and, when desired to accommodate passage of tools, obtain a view otherwise blocked by tools, etc., rotate the camera to a new position, and operate the image control system to determine the extent of the physical rotation of the camera about the axis of the cannula, while operating the image control system to rotate the displayed image to maintain the image in the preferred initial orientation. In this description, the initial orientation refers to the image obtained upon first placement of the cannula. The initial preferred orientation is the image that the surgeon prefers to work with, and uses the system to set a desired up-down orientation. It could be established by initial placement of the cannula (it could be the initial orientation), or it could be established after initial placement with the system rotating the image as desired by the user to display the initial preferred orientation on the display screen. All of the user input described can be provide through an interface, such as a dialog box in the onscreen interface, soft key provided on the display along with a keyboard, or a physical switch or button on the control system, or other input means.

The system need not know what the initial position is or where it is in absolute terms: The operator may provide input to the image control system to set, in the system, the initial preferred orientation, and thus determine the sensor reading corresponding to the initial preferred orientation. The image control system then need only determine the radial motion of the camera, vis-à-vis an initial position. For example, using the accelerometer, the surgeon will provide input to the image control system to set the initial preferred orientation (after adjusting the cannula and camera, and perhaps adjusting the image). The accelerometer readings should be zero at this point, or taken as a starting point, and the system need not determine the actual position of the camera. Subsequent rotation of the camera about an axis of the cannula tube will result in acceleration signals which are used by the image control system to determine the amount of rotation.

In embodiments where the image control system works in cooperation with a neuronavigation system, which provides absolute position relative to sensors of the neuronavigation system, the image control system may rotate images vis-à-vis an absolute position. Thus, the system may be operable to determine, after registration of system sensors with the patient, where the camera is and where it is pointed, and determine its radial position, including determining the initial radial position (when this is indicated with input from an operator) and tracking the radial position of the camera in space, rather than determining its rotation from an initial starting position.

The initial preferred orientation may be obtained by (1) initial placement and manual rotation of the cannula and camera assembly, rotating the cannula and camera assembly prior to fixing it rotationally to the body or (2) initial placement of the camera assembly without regard to orientation of the camera to obtain an image in an initial orientation (which may or may not be preferred) and subsequent operation of the image control system to rotate the image data to present an image in the initial preferred orientation on the display screen.

The image control system, associated image processing software and associated input devices provide means for adjusting the displayed image and rotating the image to an initial preferred orientation as described above. The various sensor systems described in relation to FIGS. 3A, 3B and 3C provide means for tracking the radial position of the camera. The image control system and associated image processing software provide means for presenting images obtained from the camera assembly on the display in an initial preferred orientation, and for rotating the image, in response to rotation of the camera assembly radially relative to the cannula tube, to continue to present an image of the surgical space in the initial preferred orientation.

While the preferred embodiments of the devices and methods have been described in reference to the environment in which they were developed, they are merely illustrative of the principles of the inventions. The devices may be used in various intracerebral procedures such as intra- ventricular hemorrhage procedures, neuro-stimulation procedures, and tumor resection, and various spine surgeries such as decompression and fusion procedures, and tumor resection. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of imaging a surgical field in the body of a patient, said method comprising the steps of:
   providing a cannula system for accessing a surgical field, said cannula comprising:
      a cannula comprising a cannula tube with a proximal end and a distal end and a lumen extending from the proximal end to the distal end, said proximal end of the cannula having a rim, said lumen configured to allow passage of surgical tools from the proximal end of the cannula tube to the distal end of the cannula tube; and
      a camera assembly secured to the rim of the proximal end of the cannula, with a portion of the camera assembly overhanging the lumen and extending into the lumen or a cylindrical space defined by the lumen of the cannula tube and extending therefrom;
      a display screen;
      sensing means for generating signals corresponding to a radial position of the camera assembly, relative to an axis of the cannula tube; and
      means for presenting images obtained from the camera assembly on the display in an initial preferred orientation, and for rotating the image, in response to rotation of the camera assembly radially relative to the cannula tube, to continue to present an image of the surgical space in the initial preferred orientation;
      an image control system operable to receive image data from the camera assembly and generate corresponding images for display on the display screen, and operable to display said images in an initial preferred orientation, and operable to rotate the image, in response to rotation of the camera assembly radially relative to the cannula tube, to continue to present images of the surgical space in the initial preferred orientation;
   operating the image control system to display the images in the initial preferred orientation, and rotate the images, in response to rotation of the camera assembly radially relative to the cannula tube, to continue to present images of the surgical space in the initial preferred orientation; wherein
   the image control system is configured to receive input from a user indicating that the camera assembly is in a first radial position relative to the cannula tube and rim of the proximal end of the cannula tube and display an image received from the camera assembly of the surgical field in an initial orientation corresponding to said first radial position on the display screen, and thereafter receive signals from the sensors corresponding to the radial position of the camera assembly relative to the cannula tube and rim of the proximal end of the cannula tube, and determine that the camera assembly is in a second radial position relative to the cannula tube and rim of the proximal end of the cannula tube and receive a second image from the camera assembly, and, based on this determination, rotate the second image presented on the display screen to present the second image in the initial orientation;

inserting the distal end of the cannula tube into the body of a patient, through an opening, to place the distal end of the cannula tube proximate tissue in the surgical field;

placing the camera at a first radial location relative to the opening;

provide input to the image control system through an input means, indicating that said first radial position is a first radial position;

operating the control system to present an image of the surgical field in an initial orientation corresponding to the first radial position on the display screen;

operating the control system to receive input from the sensors which are indicative of the radial position of the camera;

rotating the camera to a second radial position about the axis of the cannula tube;

operating the control system to determine the rotation of the camera about the axis of the cannula tube; and operating the control system to rotate the displayed image to maintain the image in the preferred initial orientation.

2. The method of claim 1, wherein the initial orientation refers to the image obtained upon a first placement of the cannula.

3. The method of claim 1, wherein the initial orientation is an orientation established after initial placement of the cannula system upon rotating the image as desired by the user to display the initial preferred orientation on the display screen.

* * * * *